(12) United States Patent
Benasich et al.

(10) Patent No.: US 9,320,458 B2
(45) Date of Patent: Apr. 26, 2016

(54) METHODS AND SYSTEMS FOR SCREENING AND TREATMENT OF INFANTS DEMONSTRATING DEFICITS IN AUDITORY PROCESSING

(71) Applicants: April A. Benasich, New York, NY (US); Teresa Realpe-Bonilla, Bloomfield, NJ (US); Naseem Choudhury, Mine Hill, NJ (US); Cynthia P. Roesler, Franklin Lakes, NJ (US); Jason Nawyn, Hawthorne, NJ (US)

(72) Inventors: April A. Benasich, New York, NY (US); Teresa Realpe-Bonilla, Bloomfield, NJ (US); Naseem Choudhury, Mine Hill, NJ (US); Cynthia P. Roesler, Franklin Lakes, NJ (US); Jason Nawyn, Hawthorne, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 14/611,862

(22) Filed: Feb. 2, 2015

(65) Prior Publication Data
US 2015/0190073 A1 Jul. 9, 2015

Related U.S. Application Data

(60) Continuation of application No. 13/535,447, filed on Jun. 28, 2012, now Pat. No. 8,951,206, which is a division of application No. 12/445,453, filed as application No. PCT/US2007/081328 on Oct. 13, 2007, now Pat. No. 8,231,543.

(60) Provisional application No. 60/851,851, filed on Oct. 13, 2006.

(51) Int. Cl.
A61B 5/12 (2006.01)
A61B 5/00 (2006.01)
(Continued)

(52) U.S. Cl.
CPC . *A61B 5/12* (2013.01); *A61B 5/121* (2013.01); *A61B 5/4041* (2013.01); *A61B 5/6896* (2013.01); *G09B 5/04* (2013.01); *A61B 3/113* (2013.01); *A61B 2503/04* (2013.01)

(58) Field of Classification Search
CPC ... A61B 5/121; A61B 5/6896; A61B 2503/04
USPC ......... 600/300, 544–547, 552, 558, 559, 587; 73/584, 585, 645, 656; 381/23.1, 381/312–331; 446/143, 397, 404, 491
See application file for complete search history.

(56) References Cited

U.S. PATENT DOCUMENTS

2004/0049124 A1  3/2004  Kullok et al.

FOREIGN PATENT DOCUMENTS

DE  3304009 A1  8/1984
EP  0411713 A1  2/1991
(Continued)

OTHER PUBLICATIONS

Oka et al. A VEP study on intermediate level of form vision, technical report of IEICE, Japan, the institute of electronics, Nov. 11, 2011, vol. 101 No. 513, p. 43-53.
(Continued)

*Primary Examiner* — Lee S Cohen
*Assistant Examiner* — Emily Lloyd
(74) *Attorney, Agent, or Firm* — Fox Rothschild LLP

(57) ABSTRACT

The present invention provides a method and apparatus for screening infants at high risk for central auditory processing deficits and then remediating less efficient processing behaviorally using an adaptive training algorithm that gradually increases sensitivity to rapidly occurring stimuli streams.

10 Claims, 9 Drawing Sheets

(51) Int. Cl.
*G09B 5/04* (2006.01)
*A61B 3/113* (2006.01)

(56) References Cited

FOREIGN PATENT DOCUMENTS

| JP | H10-511472 | 11/1998 |
| WO | 9618184 A1 | 6/1996 |
| WO | 2005094667 A2 | 10/2005 |
| WO | 2006/009771 A1 | 1/2006 |
| WO | WO2006/009771 A1 | 1/2006 |
| WO | 2005094667 A3 | 6/2006 |

OTHER PUBLICATIONS

Nawyn, et al. "An Operantly Conditioned Looking Task for Assessing Infant Auditory Processing Ability". Proceedings of the Ninth International ACM SIGACCESS Conference on Computers & Accessibitily (2007), pp. 147-154.

Benasich, et al. "The Importance of Rapid Auditory Processing Abilities to Early Language Development: Evidence from Converging Methodologies". Dev Psychobiol. (2002) 40(3): 278-292.

Benasich, et al. "Infant discrimination of rapid auditory cues predicts later language impairment". Behavioural Brain Research 136 (2002), pp. 31-49.

Oka et al. A VEP study on intermediate level of form vision, technical report of IEICE, Japan, the institute of electronics, Nov. 11, 2011, vol. 101 No. 513, p. 43-53, English translation of abstract only.

METHODS AND SYSTEMS FOR SCREENING AND TREATMENT OF INFANTS DEMONSTRATING DEFICITS IN AUDITORY PROCESSING

This patent application is a continuation of and claims the benefit of and priority to U.S. Pat. No. 8,951,206, filed Jun. 28, 2012, which in turn is a divisional application of and claims the benefit of U.S. Pat. No. 8,231,543, filed Apr. 13, 2009, which in turn is a national stage application of international Patent Application No. PCT/US07/81328 filed Oct. 13, 2007, which claims priority under 35 U.S.C. §119(e) to a U.S. Provisional application 60/851,851 filed on Oct. 13, 2006. The teachings of the priority applications are incorporated herein in their entireties to the extent they do not contradict to the teaching of the instant application.

FIELD OF THE INVENTION

The instant invention relates generally to methods and systems for screening and treating young infants at high risk for language learning impairment, as well as improving language learning in normally developing infants.

BACKGROUND

Early life experiences appear to have a significant and long-lasting impact on the maturing brain. Experience-dependent plasticity, during the brief, but extreme postnatal epoch of heightened nervous system receptivity commonly referred to as the critical period (Wiesel & Hubel, 1965; Simons & Land, 1987), facilitates stable perceptual biases in the adult cortex (de Villers-Sidani, Chang, Bao, Merzenich, 2007).

Longitudinal studies with infants offer insights into the etiology of Language Learning Impairment (LLI). From birth, infants possess remarkably sophisticated acoustic capabilities allowing the perception of speech as well as non-speech sounds. This phenomenon enables the study of linguistic precursors well before spoken language emerges. Levels of performance on tasks tapping these early precursors (such as rapid auditory processing) have been shown to be predictive of language skills at 16, 24, and 36 months of age.

The mechanism by which lower-level processing skills influence later language outcomes likely occurs early on in development, when acoustic and phonological maps are being constructed. Over time, the cumulative effects of poorly encoded representations may result in delay or impairment of language skills. However, if early intervention were successful in increasing efficiency of early auditory processing, it is possible that later language difficulties could be reduced or eliminated. The progress in this art is hampered due to the fact that the pool of language-related technologies for infants is quite small.

One such example is the Baby Babble-Blanket (BBB), a system developed to provide infants and developmentally delayed children with a mechanism that enables them to communicate or control their environment. When lying on the blanket, the infants use simple movements, such as head rolling or leg raising to activate digitized sounds. The BBB intervention was used to train cause-effect relationships in 5 month olds with limited physical ability, and was found to be successful at increasing switch activations in response to the sound of the mother's voice.

Another project involving infant communication is the Early Vocalization Analyzer (EVA), a program that automatically analyzes digitized recordings of infant vocalizations. The first goal of EVA is to analyze prespeech utterances in a standardized fashion to eliminate errors in human coding. By comparing the prelinguistic utterances of normal and at-risk infants with a variety of etiologies, EVA can also be used to assess and possibly predict later language difficulties. However, EVA is focused primarily on detecting spoken language disorders and does not adequately address the problems associated with identification of children at risk for receptive and expressive language deficits.

Accordingly, there remains a need for new approaches to remediation that can be used with infants. Families with a child diagnosed with a language learning disorder would be very interested in such a technique (interface) that could serve as a corrective or preventative measure for an infant sibling. Infants born into families with a history of language learning impairments are at significantly higher risk for such disorders. The public at large would be interested in an interface device that would support optimal language development.

It is estimated that roughly 20% of preschool- and school-aged children suffer from deficits in language. More than 50% of children exhibiting early impairments specific to language continue on to develop dyslexia, a disorder associated with lifelong difficulties in the literacy domain.

Therefore, there is a need in the art for methods and systems for screening young infants at risk for LLI and treatment of this disorder once it is identified.

SUMMARY OF INVENTION

The instant invention addresses these and other drawbacks of the prior art by providing, in one aspect, a method of screening or treating information processing deficiencies in a young infant comprising: a) administering to said infant a sequence of auditory stimuli comprising at least one control stimulus and at least one test stimulus, wherein the at least one control stimulus differs from the at least one test stimulus by at least one of amplitude, frequency, pitch, and duration, the at least one control stimulus and the at least one test stimulus are administered within about 1 ms to about 3 seconds of each other, the infant is habituated to the at least one control stimulus; and b) recording a response of the infant to the at least one test stimulus or the at least one control stimulus. In one set of embodiments, the response of the infant to the at least one test stimulus is an operantly-conditioned behavioral response. In some embodiments, the at least one control stimulus and the at least one test stimulus are compound stimuli comprised of a plurality of sensory components separated by filled or unfilled temporal intervals ranging from about $10^{-3}$ sec to about 1 sec, and wherein the compound stimuli are separated by temporal intervals greater than the temporal intervals separating components within one stimulus.

In another aspect, the invention provides a system for screening or treating information processing deficiencies in a young infant comprising: a) a sound-emitting device capable of emitting a sequence of auditory stimuli comprising at least one control stimulus and at least one test stimulus, wherein the at least one control stimulus differs from the at least one test stimulus by at least one of amplitude, frequency, pitch, and duration, the at least one control stimulus and the at least one test stimulus are administered within about 500 ms to about 3 sec of each other, b) a processor operably connected to the sound-emitting device; c) an input device, operably connected to the processor, capable of initiating or modifying the sequence of auditory stimuli, and capable of initiating a reinforcement stimulus in conjunction with the at least one test stimulus; and d) a recorder adapted to register a response of the young infant to the at least one test stimulus or at least one control stimulus.

In a third aspect, the invention provides a software product comprising computer program product embodied on a computer-readable medium for screening or treating information processing defects in a young infant comprising: a) a computer code for initiating an administration of a first pattern of auditory stimuli comprising at least one control stimulus and at least one test stimulus, wherein the at least one control stimulus differs from the at least one test stimulus by at least one of amplitude, frequency, duration, and pitch, the at least one control stimulus and the at least one test stimulus are administered within about $10^{-3}$ sec to about 1 sec of each other, b) a computer code for registering a response of the young infant to the at least one test stimulus or the at least one control stimulus; and c) a computer software for providing a feedback to a user of the computer program.

DETAILED DESCRIPTION OF DISCLOSED EMBODIMENTS

Figure 1:
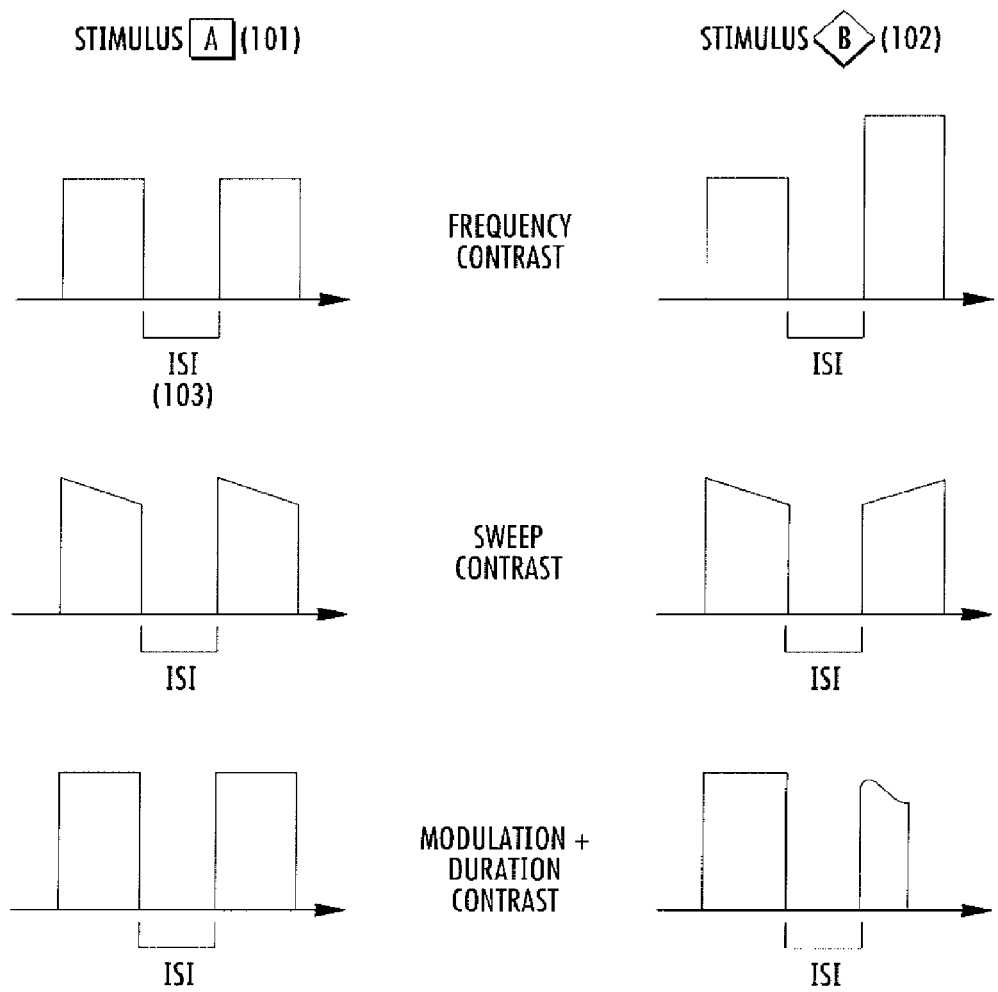
FIG. 1 illustrates examples of auditory stimuli that could be employed in the method for diagnosing and remediating deficits in auditory processing in infants.

For the purposes of better understanding of the instant invention, the following definitions are provided:

The term "deficit" or "deficiency" refers to deviations from normal responses during the administration of the methods of the instant invention. The deficit does not need to be pathological.

The term "young infant" includes a child who is younger than about two years old assuming that the child was delivered on time. If the child was delivered prematurely, such child may be older than two years by the time difference between the normal pregnancy (40 weeks) and the actual pregnancy.

The term "correct response" refers to the presence of a conditioned response to the test stimulus as well as the lack of the conditioned response to a control stimulus.

The term "recorder" refers to a device which can evaluate the response of the young infant to an auditory stimulus, and in some embodiments, may be used for tracking (such as storing and/or processing) of the responses.

The term "test stimulus" refers to a stimulus which is different from the control stimulus, wherein the response of the infant to the test stimulus is, or is expected to be, operantly-driven.

The term "control stimulus" refers to a stimulus to which the infant is expected to habituate.

The term "Passive Exposure (PE)" refers to exposing the young infant in a free field setting to the same blocks of auditory stimuli across multiple sessions.

The term "Active Behavioral training (ABT)" refers to discrimination training using an operantly-conditioned, head-turn procedure.

Patterned auditory inputs appear to play a crucial role in shaping neuronal processing and decoding circuits in the primary auditory cortex during early infancy. (Bao, 2003, Kilgard & Merzenich, 1998; Zhang et al., 2001, 2002). Thus the neural mechanisms that underlie cortical plasticity in the infancy period differ from those engaged in older children and adults and intervention techniques must be specifically geared to this age group.

The methods and systems of the instant invention may "normalize" and optimize information processing in young infants at highest risk for language-based learning impairments before language is acquired. Thus a language disorder might be ameliorated or prevented entirely from occurring. Such techniques might also support more efficient, optimal processing of incoming acoustic (and visual) information even in normally developing infants.

This invention provides the opportunity to identify infants at highest risk of poor language outcomes and to then remediate them at a very early age (below two years, or, more preferably below about 12 months, or, more preferably below about six months, or, most preferably, between about 3 and about 5 months) by improving their processing of ongoing rapid, sequential acoustic information. This early non-verbal processing is a critical substrate that must be in place for accurately setting up initial language mapping in the developing brain.

The research by the inventors suggests that such remediation is possible using a passive exposure paradigm (using the appropriate stimuli parameters) (Ortiz-Mantilla, Chojnowska, Choudhury & Benasich, 2006) with further remediation possible using a converging active paradigm (i.e. operant training) and eye-tracker guided computerized operant conditioning training.

Thus, in a broad aspect, the invention provides a method of screening and ameliorating information processing deficiencies in a young infant. Generally, such a method is accomplished in several steps. First, a pattern of control stimuli is administered to the infant. Preferably, the pattern comprises identical stimuli, namely, identical sounds. It should be understood however, that these control stimuli may be administered individually, or in groups, such as in sequences of two, three, four, etc. In the instant disclosure, purely for simplicity, the pairs of stimuli are discussed. The stimuli within one pair may be separated by an intrastimulus interval (which is also referred to as ISI) ranging from about 1 millisecond to about one second, preferably from about 10 milliseconds to about 500 milliseconds, or from about 70 milliseconds to about 300 milliseconds. The pairs of these stimuli are separated by intertrial time intervals (which is also referred to as ITI), which should be sufficiently long to allow the infant to distinguish between the consequent pairs of stimuli, typically between about 0.5 and about 3 seconds. In one embodiment, the intertrial time intervals depend on the compound control stimulus duration (CCSD) including the duration of all sensory components and all filled or unfilled intrastimulus intervals. Thus, the intertrial time interval may be calculated according to a formula ITI=X×(CCSD) wherein X is greater than 1.5. Thus, ITI is at least 1.5 times longer than CCSD, and may be 2 times longer or 3 times longer, etc., up to about 10 times longer than the CCSD. The pattern may comprise between about 2 and about 10 pairs of stimuli.

Figure 2:
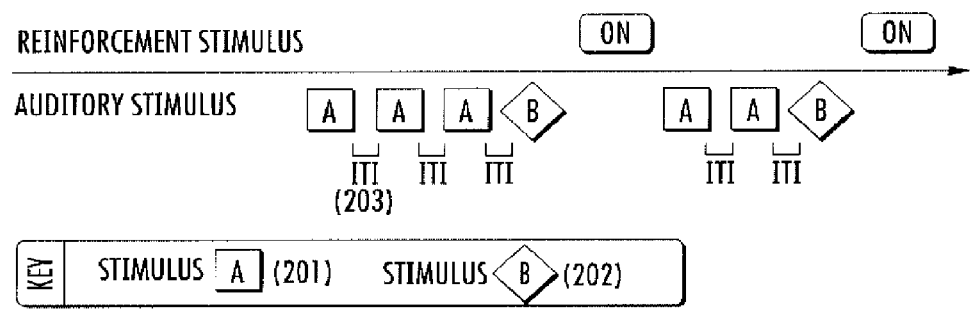
FIG. 2 illustrates an exemplary sequence of stimuli to be delivered by an apparatus embodying the invention.

Once the infant is habituated to the control stimulus, a second step is implemented. A different stimulus, namely, the test stimulus, is added into the sequence of control stimuli. In one purely illustrative embodiment shown in FIG. 1, the new sequence will comprise a compound control stimulus (Stimulus A (101)) having two identical sound components, and a compound test stimulus (Stimulus B (102)) having two components, one or more of which differ from the components of the compound control stimulus. The compound control stimulus and the compound test stimulus should differ by at least one of their respective properties, such as, for example, pitch, frequency, duration, and amplitude. In one embodiment, the test stimulus differs from the control stimulus by frequency and at least one of pitch and duration. In one exemplary embodiment illustrated in FIG. 2, compound control stimulus (Stimulus A (201)) is administered about five times more often than the compound test stimulus (Stimulus B (202)). FIG. 2 also illustrates example ITIs (203) between each presentation of stimuli. A reinforcement stimulus is administered in conjunction with Stimulus B. The design of the reinforcement stimulus depends on many variables, such as, for example, the infant's age and the infant's preferences. For example, for younger subjects (e.g., younger than 6 months), the reinforcement stimulus may comprise a video appropriate for the child's age, with a source of the reinforcement stimulus preferably located in a position which requires the child to move his eyes toward the screen playing the video. For older infants (e.g., older than six months), the source of the reinforcement stimulus may be located in a position requiring the subject to turn his or her head to the reinforcer. Alternatively, an older group (e.g., older than 9 months) may be taught to perform a task which initiates the appearance of the reinforcement stimulus upon the correct recognition of the test stimulus. For example, once the child hears the test stimulus, he/she touches a button or panel, and the reinforcement stimulus is administered (e.g., a video or a song is played).

Figure 3:
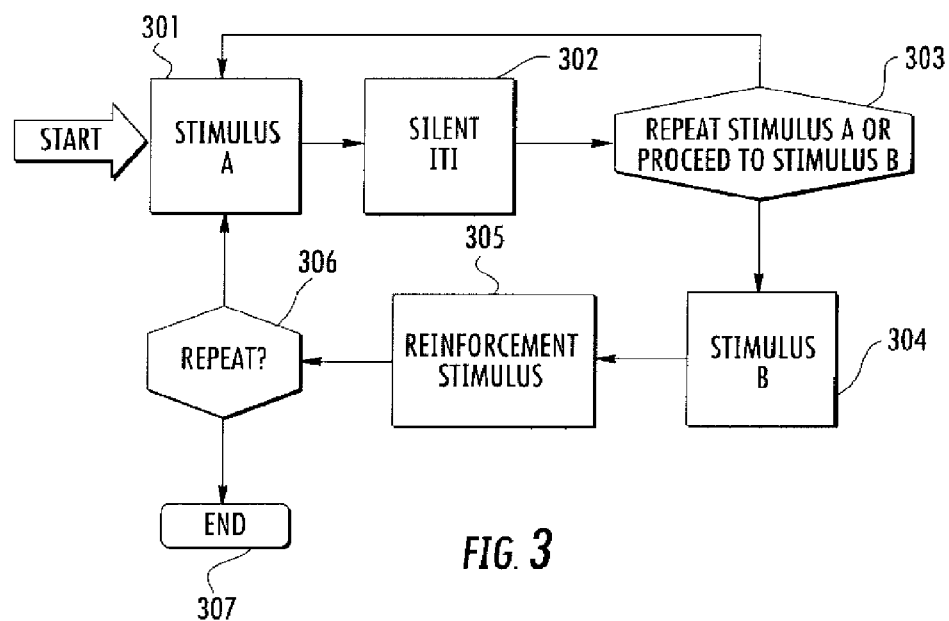
FIG. 3 is a block diagram illustrating the "Familiarization" sequence of this method.

One exemplary embodiment of the familiarization stage of the methods of the instant invention is illustrated in FIG. 3. At Block 301, auditory Stimulus A (101) is presented. Block 302 represents the silent inter-trial interval between each presentation of an auditory stimulus; the duration of the ITI remains constant within each administration of the sequence. At Decision Block 303, return to Blocks 301-302, repeating auditory Stimulus A OR proceed to Block 304. At Block 304, auditory Stimulus B (102) is presented. When auditory Stimulus B is presented, a reinforcement stimulus (Block 305) is activated immediately. When the reinforcement stimulus terminates, proceed to Decision Block 306. At Decision Block 306, the determination is made to return to Block 301 and continue the sequence OR to END (Block 307) and proceed to next sequence. The Familiarization sequence (Blocks 301 to 306) is repeated a predetermined number of times to expose the child to the pairing of auditory Stimulus B and the reinforcement stimulus. The Familiarization sequence is typically conducted before any additional sequences during an administration of the method.

Figure 4:
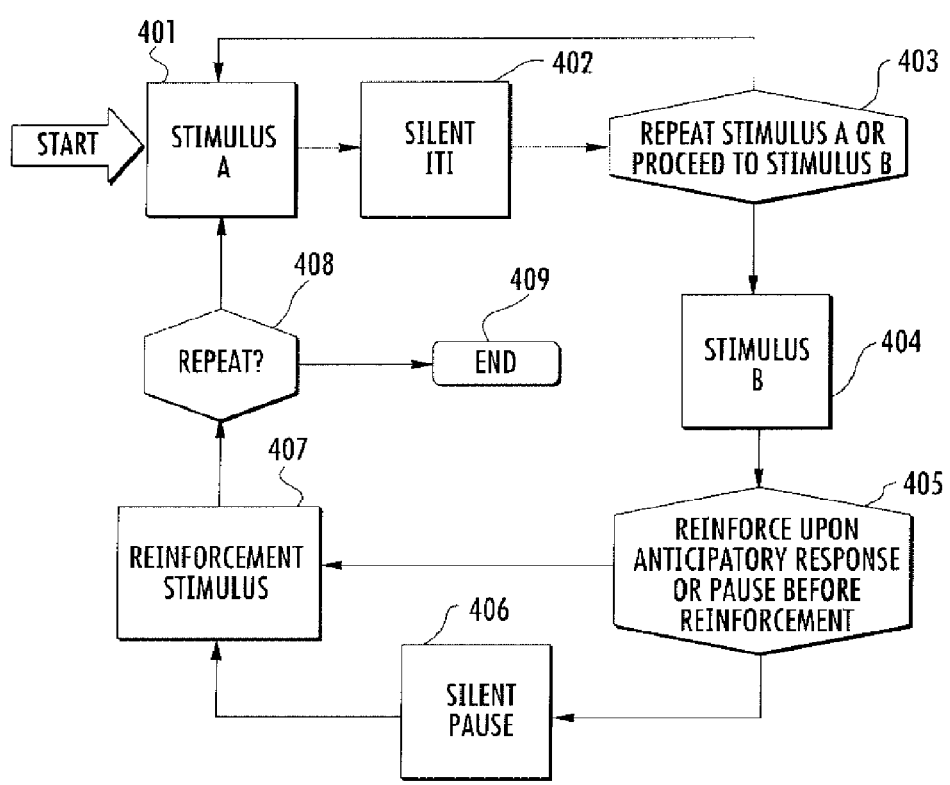
FIG. 4 is a block diagram illustrating the "Training" sequence of this method.

After the infant learns that the reinforcement stimulus accompanies the test stimulus (Stimulus B), the training phase is conducted. One embodiment of the training phase is illustrated in FIG. 4. At Block 401, auditory Stimulus A (101) is presented. Block 402 represents the silent inter-trial interval between each presentation of an auditory stimulus; the duration of the ITI remains constant within each administration of the sequence. At Decision Block 403, return to Blocks 401-402, repeating auditory Stimulus A (101) OR proceed to Block 404. At Block 404, auditory Stimulus B (102) is presented. After auditory Stimulus B is presented, proceed to Decision Block 405. At Decision Block 405, proceed to Block 406 if the child does not demonstrate the conditioned response. At Block 406 a designated silent pause time equal to that of the silent intertrial interval (402) occurs before proceeding to Block 407 where the reinforcement stimulus is presented. However, if the child anticipates the appearance of the reinforcement stimulus and correctly demonstrates a conditioned response (Decision Block 405), the reinforcement stimulus will appear immediately (Block 407). When the reinforcement stimulus terminates, proceed to Decision Block 408. At Decision Block 408, the determination is made to return to Block 401 and continue the sequence OR to END (Block 409) and proceed to next sequence. The sequence (Blocks 401 to 408) is repeated until the child correctly anticipates a predetermined proportion of test trials delivered. The same auditory stimuli, silent pause time and reinforcement stimuli are used for Familiarization (FIG. 3) and Training (FIG. 4).

Figure 5:
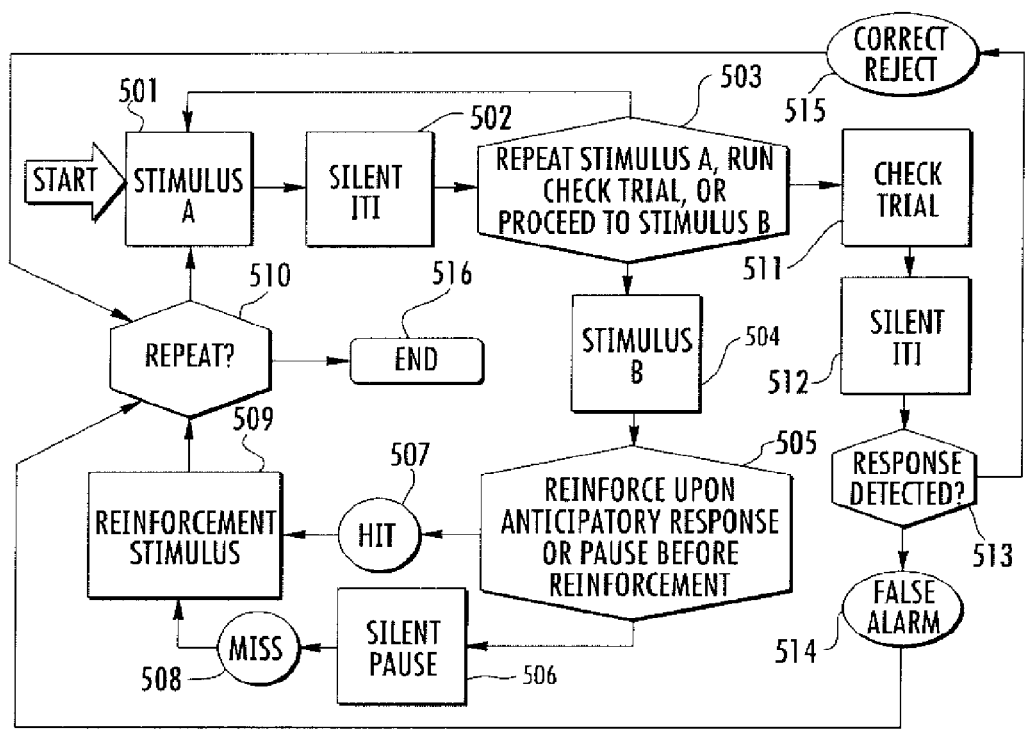
FIG. 5 is a block diagram illustrating the "Criterion" sequence of this method.

Referring to the illustration of FIG. 5, a block diagram is presented that illustrates the Criterion sequence of the method. At Block 501, auditory Stimulus A (101) is presented. Block 502 represents the silent intertrial interval between each presentation of an auditory stimulus; the duration of the ITI remains constant within each administration of the sequence. At Decision Block 503, there are three possible directions to take: return to Blocks 501-502, repeating auditory Stimulus A, proceed to Block 504 OR proceed to Block 511. At Block 504, auditory Stimulus B (102) is presented. After auditory Stimulus B is presented, proceed to Decision Block 505. At Decision Block 505, proceed to Block 506 if the child does not demonstrate the conditioned response. At Block 506 a silent pause equal in time to the silent inter-trial interval (502) occurs and Scoring Block 508 (MISS) occurs before proceeding to Block 509 where the reinforcement stimulus is presented. However, if the child anticipates the appearance of the reinforcement stimulus and correctly demonstrates a conditioned response (Decision Block 505), Scoring Block 507 (HIT) occurs and the reinforcement stimulus will appear immediately (Block 509). When the reinforcement stimulus terminates, proceed to Decision Block 510.

According to a randomized schedule, the method may deviate from the above sequence at Decision Block 503, where the sequence will flow to Block 511 at a frequency equal to the occurrence of Block 504. At Block 511, auditory Stimulus A is presented followed by a silent ITI (Block 512) identical to that of 502. If the child does not demonstrate the conditioned response during this period (Block 513), the method will record a CORRECT REJECTION in Scoring Block 515 and return to Decision Block 510. If the child does demonstrate the conditioned response during Block 512 (Block 513), the method will record a FALSE ALARM in Scoring Block 514 and return to Decision Block 510.

The sequence 501-510 is repeated until the child correctly anticipates a predetermined proportion of trials delivered, at which time the Criterion sequence is scored as PASS, and the sequence ends, Block 516. The correct responses must be a combination of HITS and CORRECT REJECTIONS wherein the percentage of these responses is significantly higher than the percentage of MISSES and FALSE ALARMS. If the child does not exceed a predetermined threshold of correct responses within a fixed number of trials, the criterion sequence is scored as FAIL, and the sequence ends, Block 516.

Figure 6:
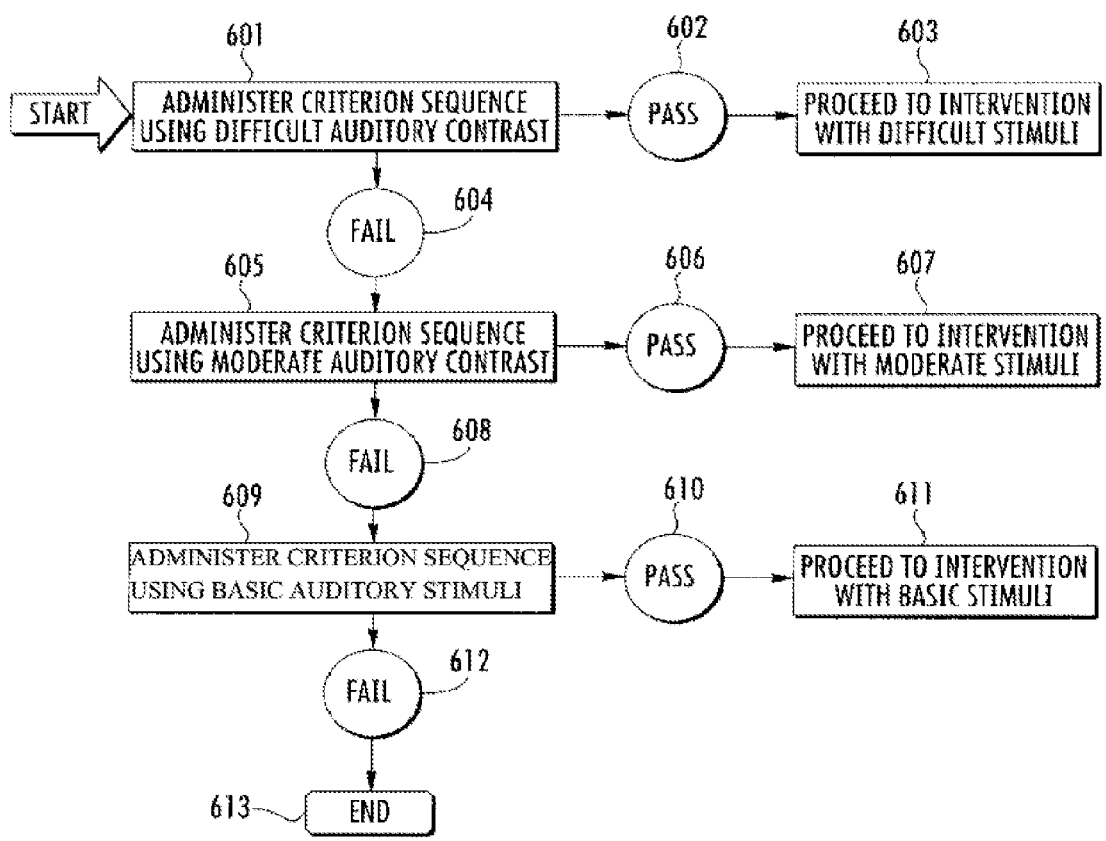
FIG. 6 is a block diagram illustrating the "Testing" sequence of this method.

Referring to the illustration of FIG. 6, a block diagram is presented that illustrates the Testing sequence of the method. For example, in an illustrative embodiment, three levels of differences are envisioned: BASIC, MODERATE, and DIFFICULT. If the tests differ by intrastimulus interval (ISI), in the BASIC difficulty level, the ISI within both the control stimulus and the test stimulus will of relatively longer duration (e.g. 300 ms); in the MODERATE level, the ISI will be of shorter duration (e.g. 100 ms); in the DIFFICULT LEVEL, the ISI will be of relatively shorter duration (e.g. 40 ms). Employing this example in reference to FIG. 6, at Block 601, administer the Criterion sequence as in FIG. 5 using auditory stimuli presented at a DIFFICULT level. If the child receives a score of PASS (602) on the Criterion sequence, proceed to Block 603 and begin the Intervention sequence (FIG. 7) using auditory stimuli presented at a DIFFICULT level. If the child receives a score of FAIL (604) on the Criterion sequence, proceed to Block 605 and administer Criterion sequence as in FIG. 5 using auditory stimuli presented at a MODERATE level. If the child receives a score of PASS (606) on the Criterion sequence, proceed to Block 607 and begin the Intervention sequence (FIG. 7) using auditory stimuli presented at a MODERATE level. If the child receives a score of FAIL (608) on the Criterion sequence, proceed to Block 609 and administer Criterion sequence as in FIG. 5 using auditory stimuli presented at a BASIC level. If the child receives a score of PASS (610) on the Criterion sequence, proceed to Block 611 and begin the Intervention sequence (FIG. 7) using auditory stimuli presented at a BASIC level. If the child receives a score of FAIL (612) on the Criterion sequence, proceed to Block 613 and discontinue session. Begin next session with Training procedure as in FIG. 4.

The final difficulty level passed during the Training sequence shall be considered the child's baseline processing index for the Intervention sequence of the method.

Figure 7:
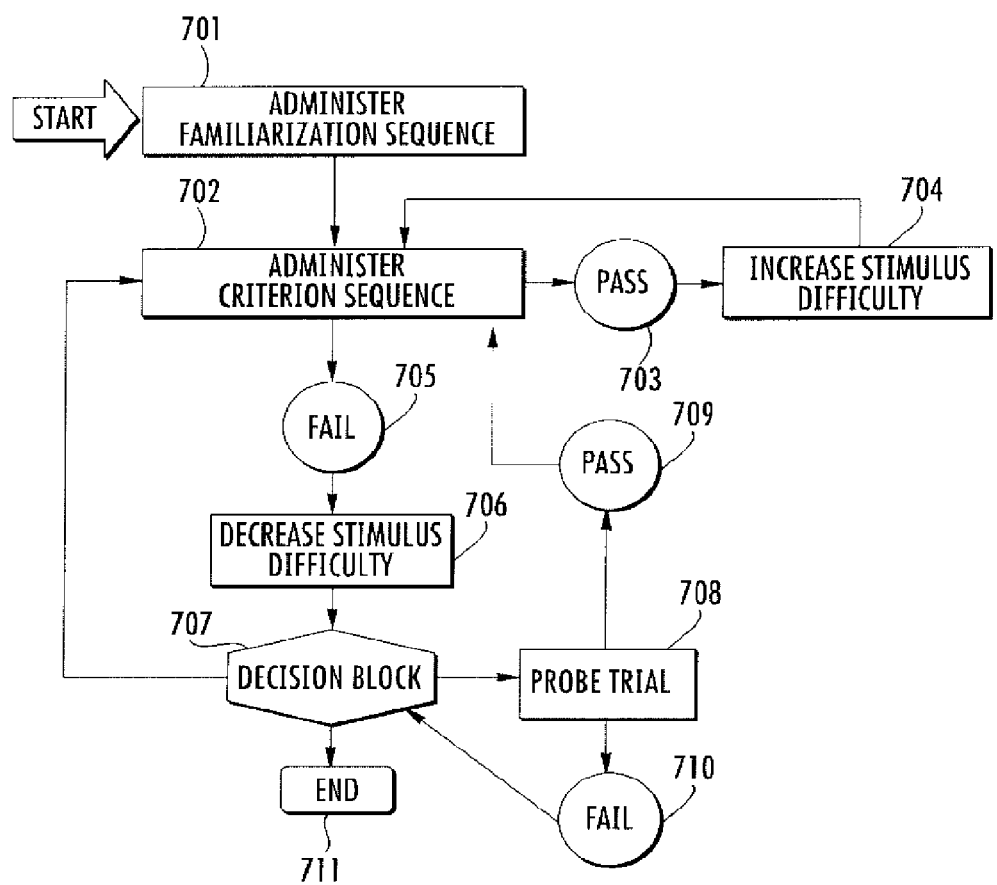
FIG. 7 is a block diagram illustrating the "Intervention" sequence of this method.

Referring to the illustration of FIG. 7, a block diagram is presented that illustrates the Intervention sequence of the method. At Block 701, administer the Familiarization sequence as in FIG. 3 using auditory stimuli at the child's baseline processing index that was determined during the Testing sequence (FIG. 6) or during a prior Intervention sequence. Proceed to Block 702 and administer the Criterion sequence as in FIG. 5. If the child passes, proceed to Scoring Block 703 and then increase the difficulty of the stimulus level by a predefined increment (Block 704). If at Block 702, the child fails the Criterion sequence, proceed to Scoring Block 705 and decrease stimulus difficulty (Block 706) according to a predefined decrement smaller than the increment in Block 704. At Decision Block 707, administer a Probe trial (Block 708) when two successive criterion blocks are failed. A probe trial consists of a Criterion sequence using the child's current baseline processing index. If child passes (Block 709), return to Block 702. If child fails (Block 710), return to Decision Block 707 and repeat PROBE trial up to two times. If child records three consecutive failures at Decision Block 707, or 5 nonconsecutive failures, proceed to Block 711 and discontinue session. Intervention sessions may be resumed at another time using the highest level of difficulty passed during the previous session.

Early life experiences appear to have a significant and long-lasting impact on the maturing brain. Experience-dependent plasticity, during the brief, but extreme postnatal epoch of heightened nervous system receptivity commonly referred to as the critical period (Wiesel & Hubel, 1965; Simons & Land, 1987), facilitates stable perceptual biases in the adult cortex (de Villers-Sidani, Chang, Bao, Merzenich, 2007).

The critical period in the auditory cortex in rat follows the onset of low-threshold hearing at P11-P12, and does not extend beyond the first month of postnatal life in rat (Zhang et al., 2001), however its onset and duration have not been determined in any other mammalian species to date including human infants. However, sensitizing infants to the rapid temporal components believed to be essential to efficient central auditory processing is more likely to be accomplished during this early critical period for experience-dependent modification of developing auditory cortex.

The mechanisms of cortical plasticity in a young infant's cortex are thought to be driven by the nucleus basalis and basal forebrain (as illustrated by rat studies), thus different neural mechanisms are engaged than those hypothesized for older children and adults.

A number of researchers have been studying the organization and plasticity of auditory cortex using animal models, primarily in rat (Bao et al, 2003; Percaccio et al., 2005; Zhang et al., 2001). Recent findings strongly suggest that there is an early "critical period" during which experience-dependent competitive modification of developing auditory cortex results in the organization of efficient temporal patterning (Katz & Shatz, 1996; Zhang et al., 2001, 2002). Specifically, patterned auditory inputs appear to play a crucial role in shaping neuronal processing and decoding circuits in the primary auditory cortex during early infancy. Thus, competitive neuronal activities play a particularly important, and instructive role in shaping neural circuits that define the spectro-temporal structures of A1 (primary auditory cortical) neurons (Zhang et al., 2001) and may do so under the control of the nucleus basalis and cholinergic projections to basal forebrain (Bao, 2003, Kilgard & Merzenich, 1998). Although the boundaries of this critical period in human infants have not yet been defined (de Villers-Sidani et al., 2007), early infancy is an ideal time to guide the developing brain to set up the precise and efficient spectro-temporal pathways that are critical for language acquisition. The research suggests that the neural mechanisms by which cortical plasticity are induced in the infancy period differ from those engaged in older children and adults.

Accordingly, the methods of this invention are advantageous when applied to young infants and believed to provide long-lasting positive influence on development of their brain, leading to better cognitive and linguistic performance. It is further believed that the young infants at risk for LLI would benefit the most from this invention. Such infants at risk for LLI may be determined on a variety of factors, including results of the testing according to certain embodiments of this invention, and/or the presence of family history of LLI, and/or the presence of prematurity or low birth weight.

The methods of the instant invention may be implemented by a variety of systems. For example, generally, the system will comprise a sound-emitting device capable of emitting the desired sound patterns as described above; a processor operably connected to the sound-emitting device; an input device, operably connected to the processor and capable of initiating or modifying the pattern of auditory stimuli and also capable of initiating a reinforcement stimulus; and a recorder adapted to register a response of the infant to the at least one test stimulus.

The sound-emitting devices suitable for the instant invention are known. A suitable non-limiting example of such is a speaker which can be connected to a personal computer, e.g., a laptop or a desktop. The input device may be a modified keyboard with multiple keys. Pushing different keys will initiate a different pattern of auditory stimulus and/or a reinforcement stimulus. The system may further comprise at least one screen. In this embodiment, the reinforcement stimulus may be, most suitably, a video (e.g., a cartoon).

The choice of the recorder of the system depends on the training procedure. For example, if the training is drawn to eye-gaze changes, a video camera or a digital camera may be used to track the eye movements. Suitable software known in the art may be used to process the images obtained by the camera. Alternatively, or in addition to the camera, physiological responses may be recorded, such as, for example, brain activity from certain regions of the brain, as described in the Examples of this disclosure. In another embodiment, eye movements or head movements may be recorded by human observer or by electrophysiological measurements of muscle activity.

In yet another embodiment, a single device may perform both the input and the recorder functions. For example, in another embodiment, the infant may be trained to touch a button or panel or perform another action in response to the test stimulus. The act of touching the button or panel at the right time will initiate a new pattern of auditory stimuli, record the correct response, and administer the reinforcement stimulus. Alternatively, if the button is pushed at an incorrect time (e.g., after the control stimulus) or if the button is not pushed at the right time, the response will be registered as an incorrect response.

In other non-limiting embodiments, the system of the invention may comprise a computing system which may be implemented in the form of a computer server, a networked set of computers, or any other suitable implementation which is known in the art or may hereafter be devised. Further, users (i.e., caregivers and infants) may interact with the system via any suitable computing system or input and/or display device (such as a personal computer, personal digital assistant, handheld computer, laptop computer, notebook computer, kiosk, cellular phone, and/or the like). Moreover, a user's computing system may eventually be connected to the system of the invention via any suitable data communications network. Communication between a user and the system may be accomplished through any suitable communication means, such as, for example, a telephone network, public switch telephone network, intranet, Internet, extranet, WAN, LAN, wireless communications, satellite communications, and/or the like. For example, the network may be a public network, which is assumed to be insecure and open to eavesdroppers. In one embodiment, the network is embodied as the Internet. In this context, the computers (e.g., user and/or system) may or may not be connected to the Internet at all times. For instance, a computer may employ a modem to connect occasionally to the Internet, or it might maintain a permanent connection to the Internet. It is noted that the network may be implemented as other types of networks, such as an interactive television (ITV) network.

Figure 8:
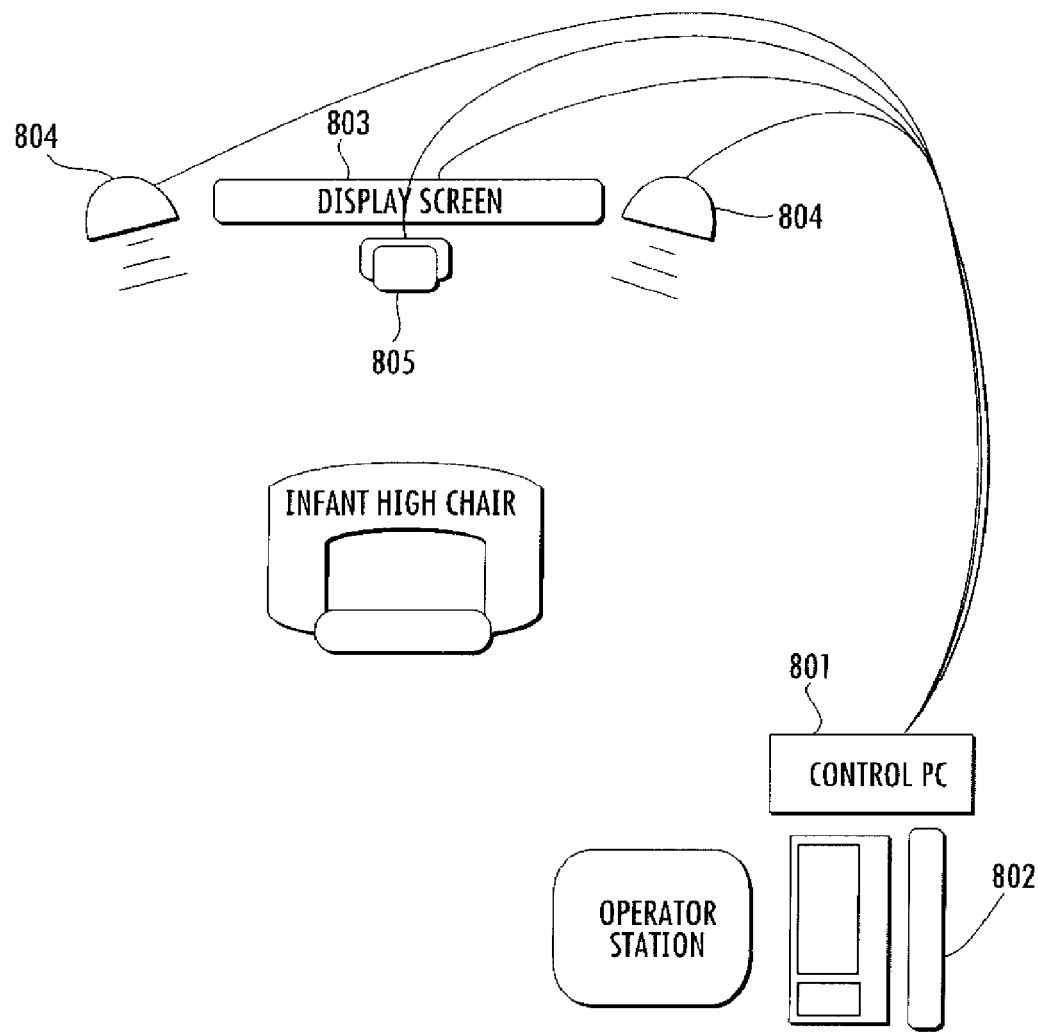
FIG. 8 illustrates an exemplary apparatus for embodiment of the invention using an automated eye gaze tracking interface.

One non-limiting example of the system of the instant invention with an automated eye gaze tracking system is illustrated in FIG. 8. This embodiment includes a microcomputer (801) with one or more display screens (802, 803), aural loudspeakers (804), an eye image camera (805), and the necessary hardware and software components to deliver the method and recognize the infant's visual point of regard by tracking movement of their eyes.

In this embodiment, the infant is seated in a high chair at an appropriate distance from the eye image camera, display screen, and loudspeakers. Auditory Stimulus A (101) and Stimulus B (102) are presented from the loudspeakers continually according to the rules of the method.

Figure 9:
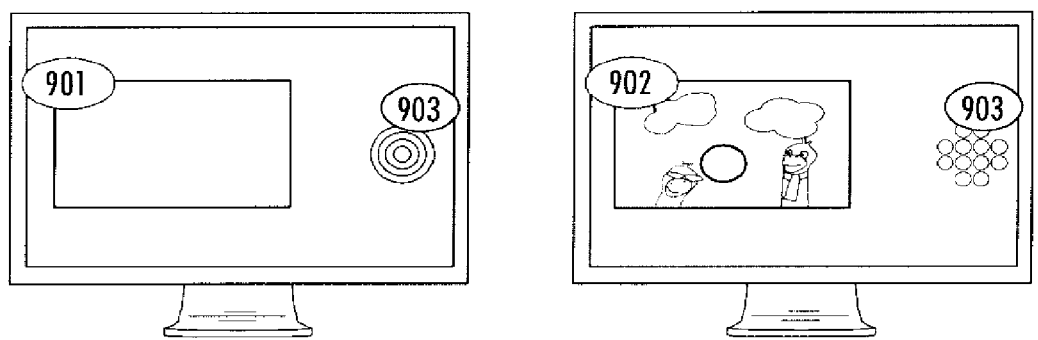
FIG. 9 illustrates a sample of visual stimuli presented to an infant in an embodiment of the invention using an automated eye gaze tracking interface.

Referring to the diagram of FIG. 9, there is shown an exemplary illustration of visual stimuli to be delivered on the display screen (803) for the embodiment using an automated eye gaze tracking system. The reinforcement stimulus used in this task is a full-color animated video segment. The reinforcement stimulus is presented in a defined area of the display screen, which is blank as shown (901) unless the rules of the method call for reinforcement.

When reinforcement is specified, the video appears as shown (902). The reinforcement stimulus display is maintained for a predetermined duration until disappearing and reverting to the state shown as 901. At all times during conduct of the method a fixation point (903) consisting of geometric patterns that may be animated, pulsing, or flashing is used to prevent the child from dwelling in the video display area (901) while the reinforcement is absent.

In additional embodiments, the system may further comprise a memory storing at least one pattern of auditory stimuli, preferably, a plurality of different patterns of auditory stimuli. In one embodiment, the response of the infant to the at least one test stimulus transmits at least a second pattern of auditory stimuli to the sound-emitting device. The advantage of this embodiment of the invention is that such a system may be included within a toy or a game. In such toy or game, the infant is taught to perform a task (e.g., to touch a button or panel or to pull a lever) when he/she recognizes the test stimulus in order to enjoy the reinforcement stimulus which, depending on the embodiment, may be a visual stimulus (e.g., a cartoon image) or an auditory stimulus (e.g. a song fragment) or any other selected positive reinforcement stimulus (e.g., moving of a toy train).

In another embodiment, the system may comprise a software program which may be implemented by a user in conjunction with any type of personal computer, personal digital assistant, handheld computer, laptop computer, notebook computer, network computer, workstation, minicomputer, mainframe, or the like, running any operating system, such as any version of Windows, Windows NT, Windows 2000, Windows 98, Mac OS, Mac OS X, Linux, UNIX, or the like. In this context, the software may be embodied in any suitable storage medium (e.g., a hard disk, CD-ROM, and/or the like) and/or may be downloadable via a communications network from another computing system.

EXAMPLES

Example 1

Passive Exposure to Rapid, Sequential Auditory Signals Modulates Cortical Response Across Time Materials and Methods Participants: 47 healthy full-term infants without reported hearing, language, or neurological problems divided in 3 groups, as summarized in Table 1.

TABLE 1

|  | N | Passive Exposure | Active Behavioral Training |
|---|---|---|---|
| Group A | 5 | ERP every month from 3-24 months Total: 32,568 standards & 5,750 deviants | At 6 & 9 m after ERP |
| Group B | 18 | ERP at 6, 12, & 24 months Total: 4,248 standards & 750 deviants | At 6 & 12 m 1 hour before ERP |
| Group C | 24 | ERP at 6, 9, 12, 16, & 24 months Total: 7,080 standards & 1,250 deviants | At 6 & 9 m after ERP |

Stimuli for the HT task were selected as follows:

70 ms complex tones with $F_o$ of 100 or 300 Hz containing 15 harmonics (6-dB roll-off per octave) with either 70, 300, or 500 ms within pair ISI.

Standard (the stimulus having two the control components)=100-100 Hz.

Target (the stimulus having the control component and the test component, respectively)=100-300 Hz.

Stimuli for the Event Related Potential ("ERP") were selected as follows"

Complex tone pairs with a fundamental frequency of 100 or 300 Hz and either a 300 or 70 ms within-pair interstimulus interval (ISI).

The low-high pairs (100-300 Hz) were presented in an oddball paradigm as deviants (15%) among low-low (100-100 Hz) standards with a between-pair interval of 700 ms.

The pairs were presented at 75 dB SPL free field via loud speakers to the left and right of the participant.

Infants were alert and awake and viewed a silent video or were entertained with a silent puppet show.

The EEG/ERP data were recorded with 62 Ag/AgCl electrodes connected within a sensor net (Electrical Geodesics, Inc.).

The EEG electrodes were referred to the vertex electrode, and re-referenced off-line to an average reference (whole head). ERP's were filtered offline with a bandpass of 0.5-25 Hz and epochs containing signals higher than +/−200 μV were discarded.

Remaining artifact free epochs were averaged by stimulus type (deviant or pre-deviant standard) for each block of trials.

The peak amplitude and latency values were extracted for the N250, P350 and MMR component at the frontal ($F_z$, $F_3$ & $F_4$), fronto-central ($Fc_z$, $Fc_3$, & $Fc_4$), central ($C_3$ & $C_4$), temporal ($T_3$ & $T_4$), parietal ($P_3$ & $P_4$), and occipital ($O_1$ & $O_2$) areas.

To investigate group differences in mean latency and amplitude a series of one-way ANOVAs were performed for 70 and 300 ms ISI conditions.

To investigate stimuli (standard and deviant) by group interactions 2×3 ANOVAs were performed for 70 and 300 ms ISI conditions.

To investigate hemisphere by group interactions 2×3 ANOVAs were performed for 70 and 300 ms ISI conditions.

Results

At 300 ms ISI:

N250: No group differences in either latency or amplitude of the standard and deviant response.

P350: Group A: Earlier P350 latency than Group B and C at frontal, fronto-central and central areas.

MMR: Group A: MMR (the mismatch-like) response appeared earlier than Groups B and C at fronto-central and central areas.

At 70 ms ISI:

N250: Group A: latency for standard (all brain regions) and deviant (anterior region) was earlier than Group B and Group C. Group B showed earlier anterior latency response for the standard stimulus and earlier temporal response for the deviant stimulus than Group C.

N250: No significant differences were found on N250 latencies for standard and deviant between left and right hemispheres.

P350: Group A had faster latencies to the deviant at frontal and fronto-central channels than either Groups B and C.

MMR: the mismatch-like response appeared earlier for Group A at the frontal area.

More detailed results of these experiments are provided in Table 2.

Table 2 shows mean (S.D.) differences in the latency (ms) of the N250 response at 70 ms ISI condition. Group A had earlier response for both standard and deviant at 24 months.

| | Group A | Group B | Group C | F | p |
|---|---|---|---|---|---|
| | | Standard | | | |
| Frontal | 246 (10) | 283 (5) | 313 (4) | 20.5 | <0.001 |
| Fronto-central | 258 (11) | 283 (6) | 312 (5) | 12.4 | <0.001 |
| Central | 253 (10) | 278 (5) | 311 (4) | 16.5 | <0.001 |
| Temporal | 247 (9) | 296 (4) | 306 (4) | 16 | <0.001 |
| Parietal | 258 (10) | 317 (5) | 327 (5) | 16.3 | <0.001 |
| Occipital | 258 (12) | 233 (6) | 322 (5) | 10.4 | <0.001 |
| | | Deviant | | | |
| Frontal | 236 (9) | 314 (5) | 320 (4) | 30.6 | <0.001 |
| Fronto-central | 227 (9) | 306 (4) | 310 (4) | 35.8 | <0.001 |
| Central | 232 (9) | 307 (4) | 321 (4) | 38.7 | <0.001 |
| Temporal | 264 (10) | 289 (5) | 326 (4) | 23.5 | <0.001 |
| Parietal | 286 (11) | 284 (5) | 305 (5) | 4.05 | 0.024 |
| Occipital | 277 (11) | 298 (6) | 299 (5) | 1.52 | 0.229 |

Figure 10:
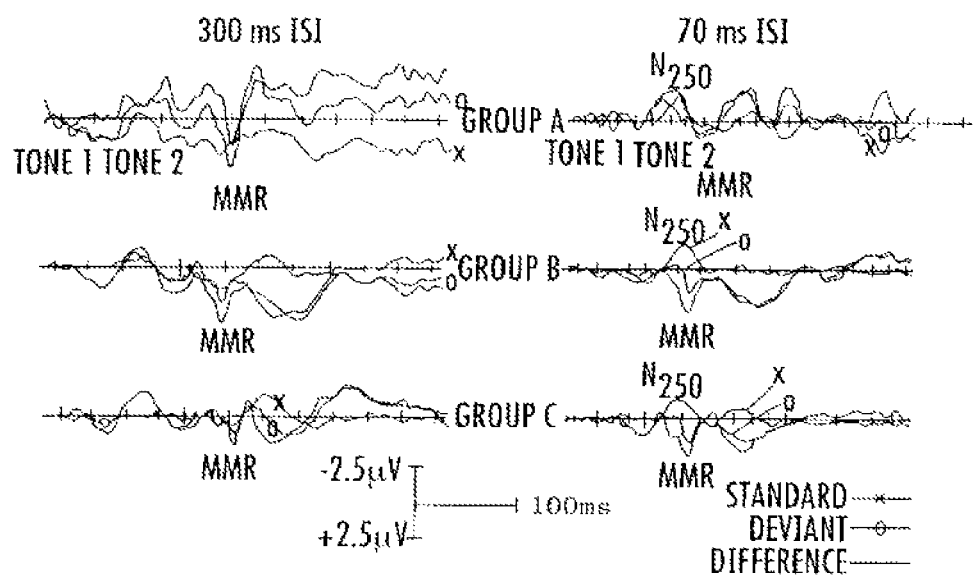
FIG. 10 illustrates brain wave responses to standard stimuli in three groups with varying passive exposure and active behavioral training to rapid sequential tones.

As shown in FIG. 10, Group A exhibits earlier response to the standard stimulus in the 70 ms ISI condition, as measured in left central area at 24 months.

Figure 11:
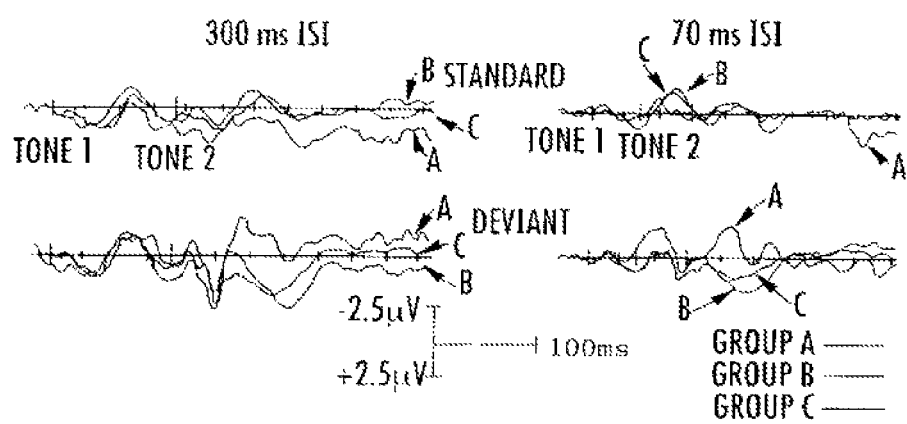
FIG. 11 illustrates brain wave responses to standard and deviant stimuli in three groups with varying passive exposure and active behavioral training to rapid sequential tones.

As shown in FIG. 11, Group A exhibits earlier and more robust response to deviant stimuli presented in the 70 ms ISI condition, as measured in left central area at 24 months.

Taken together, these data indicate that cumulative passive exposure to the same rapid, sequential auditory signals appears to modulate cortical response across time, specifically increasing processing efficiency (i.e. decreasing latency and increasing amplitude) for both slow and fast auditory discriminations. However, the strongest facilitatory effect is observed for fast successive auditory signals, a critically important substrate for early language acquisition. Evidence was also seen that the timing of active behavioral training might further enhance processing efficiency. The observed group differences might represent a longer-term priming effect or might reflect refining of the representational map used to make these types of discriminations.

Example 2

Hardware Configuration

The system consists of the main components illustrated in FIG. 8: a remote eye tracking system with pan-tilt optics and magnetic head tracker from Applied Science Laboratories (Model 504), a designated PC for controlling the eye tracker, and a second PC for controlling the assessment software. The specific interaction sequence for the task is dependent on the infant's behavior, which was determined from point-of-regard coordinates transmitted at 60 Hz over a serial data link from the eye tracker control unit.

Visual stimuli used in this task were presented on a 24" wide-aspect LCD monitor located 28" from the subject's head when seated in an infant high chair. The display area distends approximately 40° of visual angle horizontally and 25° vertically. To reduce the likelihood that subjects were distracted by objects in the testing environment, the ambient lighting is dimmed to a level of approximately 10 lux at the stimulus display screen.

During the current system evaluation phase, a minimum of two operators were present to ensure that the system is functioning properly. A third operator in an adjacent observation room provided manual blind-coding of infant gaze using a video feed from an infrared camera located at midline below the stimulus display. A parent or caregiver was seated next to (but out of sight from) the infant to attend to any needs that might arise.

Example 3

Task Configuration

The overall design of the assessment represents a careful balance among several key elements that must be in place before an operant conditioning procedure will be successful. Specifically, these are (1) a conditioned stimulus cue that will be used to signal an upcoming reward, (2) the reward stimulus itself, a display that is reinforcing enough to attract the child's attention and motivate sustained engagement with the task, and (3) an operant response by which the infant indicates anticipation of the reward.

a. Conditioned Stimulus (Audio)

Because the goal of this application is to evaluate the infant's ability to process incoming auditory information, a pair of contrastive sounds is used in creating the conditioned stimulus. These two sounds should typically differ on a single acoustic property so that modifying this parameter can result in an array of exemplars that range from very similar to very different. Depending on the specific research questions being explored, such parameters might include frequency, complexity, modulation, amplitude, or various phonological properties of speech.

In the operant conditioning task, one sound is designated as the familiar stimulus, and shall remain acoustically invariant. The familiar stimulus is presented repeatedly with a silent inter-trial interval (ITI) of 1.5 s between the offset of one instance and the onset of the next. Although the precise ITI may be adjusted based on the nature of the sounds in use, it should be short enough to enable efficient testing, but long enough to ensure the stimuli are processed as discrete units. With an appropriate ITI selected, it is expected that the infant will habituate quickly to the familiar stimulus.

The second sound is designated the novel stimulus, and is presented in place of the familiar stimulus at a ratio of approximately 1:5 per recommendations of prior work. It is the novel stimulus that is used initially to alert the child to an upcoming reward as discussed below. Over time the acoustic parameters of the sound can be varied systematically to establish a rough index of the minimal difference the infant is able to detect.

b. Reward Stimulus (Video)

The reward used in this task is a full-color animated video segment selected from a collection of age-appropriate DVD titles. The video is presented silently to the left of the display screen in a defined area representing 25 by 15 degrees of visual angle. Reference 901 of FIG. 9 shows the blank video display area as it appears during trials with the familiar audio stimulus.

During novel stimulus trials, the video will appear as shown by 902 of FIG. 9. The reward display lasts 4 seconds before disappearing. The DVD continues to play in the background even when the reward is not visible, so the exact video segment the child will view is varied and non-deterministic. The reward stimulus should be of sufficient complexity and duration to attract the child's attention, but not so stimulating that it interferes with the ability to learn the task.

c. Operant Response

A key premise of this task is whether the infant is able to learn the association between the conditioned (novel) stimulus and the onset of the video reward. Successful learning of this contingency is demonstrated when the infant directs his or her gaze into the video display area after the novel stimulus is presented, but before the reward appears.

To ensure that the subject is not simply staring into the video display area and waiting for the reward to appear, the experimental software will not deliver a novel trial unless the child's gaze is outside the defined area. A fixation point 903 consisting of geometric patterns that may be animated, pulsing, or flashing is used to distract the child from dwelling in the video area during familiar trials.

Example 4

Task Sequence

The timeline in FIG. 2 illustrates what a 30 second sample of the task might look like. The familiar (F) audio stimulus recurs 2 to 7 times between each novel (N) trial. If the infant correctly demonstrates the operant response after hearing the novel sound, the video reward is activated immediately. If no response is detected, the system will repeat the novel stimulus up to two times. If no response is received after the second repetition, the system will play the video regardless of infant behavior, thereby reinforcing or reawakening the association between the novel stimulus and the reward. The frequent presentation of the reward video also serves as a short "break" designed to increase the overall amount of time the infant will remain engaged with the task.

Example 5

Administration Protocol

The operantly conditioned looking task is embedded into an experimental research protocol designed to establish whether the infant can discriminate between the two sounds, and if he/she is able to learn the operant contingency. Stimuli for the HT task were selected as follows: a three-phase protocol similar to those used in other operantly conditioned tasks is employed in this study.

a. Training Phase

The first phase of evaluation is used to condition the association between the novel stimulus and the reward. To ensure that the infant can differentiate between the two auditory stimuli, exemplars with the greatest acoustic separation (i.e. the most discriminable) are used. A total of 10 change trials are presented. The term "change trials" is simply the name given to those instances wherein the novel stimulus is followed by the reward.

Early in this phase, it is expected that the infant will orient to the video display area only after delivery of the reward, which occurs 1.5 seconds (the length of a standard inter-trial interval) after the second repetition of a novel stimulus. The period of time between the offset of the first novel presentation and the onset of the video is called the scoring interval. As training progresses, infants who learn the stimulus-reward contingency will typically begin looking toward the video area at some point during the scoring interval. This response is scored as a 'hit' and is reinforced by the immediate activation of the video. Change trials in which the infant does not exhibit looking in anticipation of the reward are scored as a 'miss.'

Infants who score 4 or more hits on the last 6 change trials are considered to have trained on the task, and will proceed to the criterion phase. At the discretion of the test administrator, children who did not meet this baseline may repeat the training phase or proceed to criterion.

b. Criterion Phase

The second phase of evaluation is similar to the training phase, except with the introduction of 10 no-change trials interspersed among the change trials. From the infant's perspective, a no-change trial is simply an instance of the familiar stimulus. What differs from the researcher's perspective is the addition of a scoring interval to the familiar stimuli. No-change trials allow the researcher to determine whether the hits generated from the change trials represent correct performance or a looking bias in favor of the video display area. If the infant looks to the reward area during the no-change scoring interval, the trial is scored a 'false alarm.' Otherwise it is scored a 'correct rejection.'

According to traditional infant performance metrics, the participant could be considered to have passed criterion when he or she scores at least two hits and two correct rejections on 5 consecutive trials. Upon satisfying this "4/5 rule", the child may move directly into the test phase. In the current protocol, however, all 20 criterion trials are administered and scored regardless of performance.

c. Testing Phase

The testing phase proceeds similarly to the criterion phase, except that the acoustic separation between the two auditory stimuli is reduced. Depending on the infant's state, up to two 20-trial testing phases can be administered, each with a different level of difficulty. Performance at each difficulty level is reported in terms of the percentage of all trials scored correctly (either hits or correct rejections). Correct percentages above 60% are typically considered suggestive of the fact that the child was able to learn the task and perform the discrimination. Higher values indicate greater confidence that the subject's performance was above chance: at 70%, $t(19)=-2.179$, $p<0.05$; at 80%, $t(19)=-2.854$, $p=0.01$.

Example 6

Evaluation

After a brief meet-and-greet session during which the caregiver filled out a consent form and short questionnaire, the infant was seated in the high chair and positioned for optimal viewing. During this time, a silent animated video is presented on the stimulus screen.

The video is then repositioned and rescaled in a looming stimulus calibration procedure to verify whether the default eye tracker calibration will be adequate for the assessment task. For most infants it is. If not, up to two saved calibrations are tested before a 2-point "quick" calibration is attempted. If the quick calibration fails, a 9-point "full" calibration is used as a last resort. As a rule, we strive to keep the calibration phase as short as possible to conserve the infant's energy for the experimental procedure.

Once calibrated, the infant was immediately transitioned into the three-phase assessment procedure. Because our intentions at this time were to evaluate the efficacy of the operant looking task rather than study infant processing ability, a relatively simple auditory contrast was used. This strategy helps simplify interpretation of the outcome data by reducing the possible confounding effects that a difficult stimulus might introduce.

Stimuli were constructed as pairs of sinusoidal complex tones with fundamental frequencies of either 800 or 1200 Hz. Each tone included the first 15 harmonics with a 6 dB roll-off per octave. The duration of each tone is 70 ms. The familiar stimulus consisted of two 800 Hz tones separated by a short inter-stimulus interval (ISI). The novel stimulus consisted of one 800 Hz tone and one 1200 Hz tone separated by an equivalent IST. Similar tone-pair stimuli have been used in work with infants, and have been shown via electrocortical event-related potentials to be discriminable by infants without a family history of language learning disorders.

All sounds were presented at 72 dB SPL from stereo speakers located at each side of the stimulus display screen. The acoustic parameter that was varied between test phases was the duration of the inter-stimulus interval. For training and criterion, an ISI of 200 ms was used, as this slow presentation rate is likely to be discriminable by all infants. For the two testing phases, more challenging ISIs of 60 ms and 100 ms were used for Test 1 and Test 2 respectively. To control for likely fatigue effects, the order in which these were presented was counterbalanced.

In order to evaluate how much time infants are willing to spend in the task, we sought to administer as much of the assessment as possible for each child. In practice this meant that most subjects reached a point where their state precluded further testing. Either during the experimental session or afterwards based on video review, the researchers annotated the points in time during which the child's attention was considered alert versus distracted.

After concluding the looking task assessment, the participants were led to another room where a standardized intelligence test was administered.

Example 7

Results

For the research protocol described above, 21 infants under 12 months of age were entered into the evaluation study. Of these, 3 could not be tested satisfactorily due to reasons of temperament, state, technical failure, or methodological irregularities. Of the remaining 18 participants (12 male, 6 female), the mean age was 6 m 2 d. All were found to be within the normal IQ range on the Bayley Scales of Infant Development (4$^{th}$ Edition). The population mean for this study was 105 with a standard deviation of 12.4.

Table 3 presents summary data for each of the pilot participants. For criterion and testing phases, the values presented refer to the percentage of correct responses for the total number of trials administered.

TABLE 3

Data from pilot infants.

| ID | Age | Sex | Training | Criterion | Test1 | Test2 |
|----|-----|-----|----------|-----------|-------|-------|
| 1 | 2 m 25 d | M | Pass | 90%** | [1]65% | 55% |
| 2 | 3 m 14 d | F | Pass | 60% | 50% | |
| 3 | 3 m 16 d | M | Pass | 65% | [1]80%** | 65% |
| 4 | 3 m 28 d | F | Pass | 75%* | | 70%* |
| 5 | 4 m 15 d | M | Pass | 60% | | |
| 6 | 4 m 18 d | F | Pass | 80%** | 50% | |

TABLE 3-continued

Data from pilot infants.

| ID | Age | Sex | Training | Criterion | Test1 | Test2 |
|---|---|---|---|---|---|---|
| 7 | 5 m | M | Pass | 80%** | 75%* | |
| 8 | 5 m 15 d | F | Pass | 75%* | | 70% |
| 9 | 5 m 16 d | M | Pass | 70%* | | |
| 10 | 5 m 19 d | M | Pass | 80%** | | 60% |
| 11 | 5 m 22 d | M | Pass | 75%* | 75%* | |
| 12 | 5 m 23 d | M | Pass | 65% | | |
| 13 | 6 m 14 d | M | Fail | 50% | [1]55% | 65% |
| 14 | 6 m 26 d | M | Pass | 80%** | 60% | |
| 15 | 8 m 10 d | M | Pass | 75%* | | 55% |
| 16 | 10 m 16 d | F | Fail | 65% | | 55% |
| 17 | 11 m 15 d | F | Pass | 65% | | |
| 18 | 11 m 21 d | M | Pass | 90%** | 65% | |
| | | | Mean | 71%** | 64%** | 63%* |

The sign  indicates $p < 0.05$; the sign  indicates $p \leq 0.01$.
[1]First of two tests admistered.

Overall, 89% of the participants passed the training phase. Under a formal administration protocol, those subjects who failed training would not have proceeded to criterion and testing. These phases were nonetheless administered in the current evaluation to investigate other research questions. The experimental sessions were not terminated until all phases were administered or the infant's state became uncooperative. Fourteen out of 18 infants were calm enough after criterion to receive at least one test administration. Only three of these went on to receive the second test administration.

Group performance on the criterion phase was found to be significantly higher than chance ($t(16)=-8.796$, $p<0.001$), with 11 of the 16 individuals (69%) who passed training performing significantly above chance. When subjected to the traditional 4/5 rule for criterion, 100% of the trained individuals demonstrated passing performance.

Performance on test phases 1 and 2 was lower than that observed for criterion, but was still significantly higher than chance ($t(14)=-4.750$, $p<0.001$). No significant differences were observed between ISI test conditions.

On average the complete experimental protocol lasted 11 minutes from the time the infant was placed in the high chair until the session was terminated. This total includes all phases of task administration in addition to time spent on setup, calibration and interaction with the infant. When broken down according to test phases, mean durations were as follows: Training—2 m 15 s, Criterion—3 m 14 s, Testing—3 m 10 s per block.

Example 8

Quantitative Analysis

The proportion of subjects passing the training phase supports the conclusion that an infant can be conditioned to demonstrate anticipatory looking in response to changes in a continuous auditory stream. The high percentage of correct trials observed during the criterion phase suggests further that the operant response is selective to novel auditory stimuli rather than representing a general anticipatory bias.

A within-subjects analysis of the criterion phase also revealed a more nuanced pattern of responses when grouped by age: 2-3 months, 4-5 months, and 6-11 months. Although overall performance was similar for all groups, the youngest infants tended to perform better in the second half of the trials, while the oldest performed better in the first half. Subjects in the middle group performed consistently in both halves.

This observation appears to suggest that younger infants require more time to learn the task, but that they can perform well once they do. In contrast, the oldest infants seem to master the task quickly but then lose interest. Given that optimal performance pattern would be one that is consistent over time, this evidence suggests that the current task may be best suited for individuals aged 4-5 months.

All cited publications are hereby incorporated by reference in their entirety.

While the foregoing specification teaches the principles of the present invention, with examples provided for the purpose of illustration, it will be appreciated by one skilled in the art from reading this disclosure that various changes in form and detail can be made without departing from the true scope of the invention.

The invention claimed is:

1. A system for screening information processing deficiencies or improving information processing in an infant comprising:
    a processor operably connected to a sound-emitting device and an input device, wherein the processor is configured to:
    generate a first sequence of auditory stimuli comprising at least one control stimulus having a plurality of control components and at least one test stimulus having a plurality of test components, wherein the at least one control stimulus differs from the at least one test stimulus by at least one of amplitude, frequency, pitch, and duration, the at least one control stimulus and the at least one test stimulus are administered within about 0.5 seconds to about 3 seconds of each other, and
    receive from the input device an indication of one or more of the following: an initiation or modification of the first sequence of auditory stimuli, and a reinforcement stimulus in conjunction with the at least one test stimulus;
    a recorder adapted to register a response of the infant to the at least one test stimulus or the at least one control stimulus, wherein the recorder is operably connected to the input device,
    wherein the sound emitting device is configured to emit the first sequence of auditory stimuli,
    wherein the processor is configured to modify a duration of a filled temporal interval or an unfilled temporal interval between the control or test components in the at least one control stimulus or the at least one test stimulus based on the response of the infant.

2. The system of claim 1, further comprising a memory containing a plurality of sensory components, wherein the processor is further configured to combine or modify the sensory components to produce a plurality of sequences of auditory stimuli, and wherein the memory is operably connected to the processor.

3. The system of claim 2, wherein the memory comprises the plurality of the sequences of auditory stimuli, and wherein the processor is further configured to transmit at least a second sequence of auditory stimuli to the sound-emitting device in response to receiving the response of the infant to the at least one test stimulus.

4. The system of claim 2, wherein the memory comprises the plurality of the sequences of auditory stimuli, and wherein the processor is further configured to transmit at least a second sequence of auditory stimuli that is identical to the first sequence of auditory stimuli to the sound-emitting device in response to receiving the response of the infant to the at least one test stimulus.

5. The system of claim 4, wherein the processor is further configured to initiate at least the second sequence of auditory stimuli based on an incorrect response of the infant.

6. The system of claim 2, wherein the processor is further configured to transmit at least a second sequence of auditory stimuli to the sound-emitting device in response to receiving the response of the infant to the at least one test stimulus, wherein at least the second sequence of auditory stimuli is different from the first sequence of auditory stimuli, wherein at least the second sequence of auditory stimuli comprises at least one control stimulus and at least one additional test stimulus, and wherein the at least one additional test stimulus differs from at least one test stimulus by at least one characteristic selected from the group consisting of frequency, duration, pitch and amplitude.

7. The system of claim 2, wherein the processor is further configured to transmit at least a second sequence of auditory stimuli to the sound-emitting device in response to receiving the response of the infant to the at least one test stimulus, wherein at least the second sequence of auditory stimuli is different from the first sequence of auditory stimuli, wherein at least the second sequence of auditory stimuli comprises at least one control stimulus and at least one additional test stimulus, wherein the at least one additional test stimulus differs from at least one test stimulus by at least one characteristic selected from the group consisting of frequency, duration, pitch and amplitude, and wherein a difference between the at least one control stimulus of at least the second sequence of auditory stimuli and the at least one additional test stimulus of at least the second sequence of auditory stimuli is larger than a difference between the at least one control stimulus of the first sequence of auditory stimuli and the at least one test stimulus of the first sequence of auditory stimuli.

8. The system of claim 1, wherein:
the sound-emitting device is further configured to emit a sequence of auditory stimuli comprising at least one control stimulus having a plurality of control components and at least one test stimulus having a plurality of test components, wherein a number of control components in the at least one control stimulus is identical to a number of test components in the at least one test stimulus,
the processor is further configured to modify a duration of a filled temporal interval or an unfilled temporal interval between the control or test components in the at least one control stimulus or the at least one test stimulus based on the response of the infant such that the duration of the filled or unfilled temporal interval in the at least one control stimulus is identical to the duration of the filled or unfilled temporal interval in the at least one test stimulus.

9. A toy for screening information processing deficiencies or improving information processing in an infant comprising:
a processor operably connected to a sound-emitting device and an input device, wherein the processor is configured to:
generate a sequence of auditory stimuli comprising at least one control stimulus having a plurality of control components and at least one test stimulus having a plurality of test components, wherein the at least one control stimulus differs from the at least one test stimulus by at least one of amplitude, frequency, pitch, and duration, the at least one control stimulus and the at least one test stimulus are administered within about 0.5 seconds to about 3 seconds of each other, and
receive from the input device an indication of one or more of the following: an initiation or modification of the sequence of auditory stimuli, and a reinforcement stimulus in conjunction with the at least one test stimulus;
a recorder adapted to register a response of the infant to the at least one test stimulus or the at least one control stimulus, wherein the recorder is operably connected to the input device,
wherein the sound emitting device is configured to emit the sequence of auditory stimuli,
wherein the processor is configured to modify a duration of a filled temporal interval or an unfilled temporal interval between the control or test components in the at least one control stimulus or the at least one test stimulus based on the response of the infant.

10. A system for screening information processing deficiencies or improving information processing in an infant comprising:
a processor configured to generate a sequence of auditory stimuli comprising at least one control stimulus having a plurality of control components and at least one test stimulus having a plurality of test components, wherein the at least one control stimulus differs from the at least one test stimulus by at least one of amplitude, frequency, pitch, and duration, the at least one control stimulus and the at least one test stimulus are administered within about 0.5 seconds to about 3 seconds of each other;
one or more speakers in communication with the processor, wherein the one or more speakers are configured to emit the sequence of auditory stimuli, and
a camera operably connected to the processor, wherein the camera is configured to track movement of an infant's eyes in response to the at least one test stimulus or the at least one control stimulus;
wherein the processor is configured to modify a duration of a filled temporal interval or an unfilled temporal interval between the control or test components in the at least one control stimulus or the at least one test stimulus based on the movement.

* * * * *